(12) United States Patent
Kawabata et al.

(10) Patent No.: US 11,311,363 B2
(45) Date of Patent: Apr. 26, 2022

(54) TOOTHBRUSH AND SYSTEM

(71) Applicant: OMRON HEALTHCARE Co., Ltd., Kyoto (JP)

(72) Inventors: Yasuhiro Kawabata, Kyoto (JP); Hideyuki Yamashita, Kyoto (JP); Toshihiko Ogura, Kyoto (JP); Hideaki Yoshida, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 47 days.

(21) Appl. No.: 16/261,973

(22) Filed: Jan. 30, 2019

(65) Prior Publication Data

US 2019/0167399 A1 Jun. 6, 2019

Related U.S. Application Data

(63) Continuation of application No. PCT/JP2017/022421, filed on Jun. 16, 2017.

(30) Foreign Application Priority Data

Aug. 30, 2016 (JP) .............................. JP2016-167921

(51) Int. Cl.
*A61C 17/22* (2006.01)
*A46B 15/00* (2006.01)
(Continued)

(52) U.S. Cl.
CPC ............ *A61C 17/221* (2013.01); *A46B 15/00* (2013.01); *A46B 15/0036* (2013.01); (Continued)

(58) Field of Classification Search
CPC ....... A61C 17/221; A61C 17/22; A61C 19/04; A61C 1/00; A46B 15/00; A46B 15/0036; (Continued)

(56) References Cited

U.S. PATENT DOCUMENTS 5,382,163 A 1/1995 Putnam
6,485,300 B1 * 11/2002 Muller ............... A46B 15/0036
433/29
2013/0141558 A1* 6/2013 Jeon ......................... G01J 1/58
348/77

FOREIGN PATENT DOCUMENTS

JP 2002515276 A 5/2002
JP 2013-248220 A 12/2013
(Continued)

OTHER PUBLICATIONS

International Search Report dated Sep. 12, 2017 in corresponding International Application No. PCT/JP2017/022421; 4 pages.
(Continued)

*Primary Examiner* — Katina N. Henson
(74) *Attorney, Agent, or Firm* — Maier & Maier, PLLC

(57) ABSTRACT

A toothbrush of the present invention includes: a main body including a head portion having a bristle raising surface on which bristles are provided in a standing manner; a light emission unit configured to emit light through a specific region of the bristle raising surface to a tooth surface; and a light reception unit configured to receive radiated light from the tooth surface resulting from the light through the specific region, the light emission unit and the light reception unit being provided in the main body. The toothbrush also includes a detection unit configured to collectively detect whether or not dental plaque or dental calculus is present on the tooth surface based on an output from the light reception unit. The toothbrush further includes a determination unit configured to determine that dental calculus is present on the tooth surface.

6 Claims, 10 Drawing Sheets

(51) Int. Cl.
*A61C 19/04* (2006.01)
*A61B 5/00* (2006.01)

(52) U.S. Cl.
CPC ........ *A46B 15/0038* (2013.01); *A61B 5/0088* (2013.01); *A61C 17/22* (2013.01); *A61C 19/04* (2013.01); *A46B 2200/1066* (2013.01); *A61C 17/225* (2013.01)

(58) Field of Classification Search
CPC ..... A46B 15/0038; A61B 5/0093; A61B 6/14; G01J 5/10
USPC ..................................... 433/215, 29; 15/105
See application file for complete search history.

(56) References Cited

FOREIGN PATENT DOCUMENTS

WO 2009/139110 A1 11/2009
WO WO-2014097022 A1 * 6/2014 ........... A61C 17/221

OTHER PUBLICATIONS

Japanese Office Action dated Jul. 7, 2020, in connection with corresponding JP Application No. 2016-167921 (6 pp., including machine-generated English translation).

* cited by examiner

TOOTHBRUSH AND SYSTEM

FIELD

The present invention relates to a toothbrush, and more specifically relates to a toothbrush that emits light to a tooth surface and detects whether or not dental plaque and/or dental calculus is present on the tooth surface based on radiated light (particularly fluorescent light) from the tooth surface.

The present invention also relates to a system including such a toothbrush.

BACKGROUND

Conventionally, a dental plaque detection apparatus that compares the intensity of fluorescent light from a tooth surface on which substantially no biological deposit (e.g., dental plaque, bacteria, dental calculus, and calculus) is present and the intensity of fluorescent light from a test tooth surface and thus detects whether or not a biological deposit is present on the test tooth surface as disclosed in Patent Literature 1 (JP 2002-515276A), for example, has been known as such a type of dental plaque detection apparatus.
Patent Literature 1: JP 2002-515276A

SUMMARY

Dental plaque is a mass of bacteria and metabolites, and turns into dental calculus when it gradually alters and deposits on a tooth surface. Therefore, it is difficult to physically distinguish dental plaque from dental calculus completely. In short, regarding dental plaque and dental calculus, it can be said that a substance that cannot be removed by toothbrushing (brushing) is dental calculus.

Here, when it is detected whether or not a biological deposit is present on a tooth surface based on merely fluorescent light intensity as disclosed in Patent Literature 1, it is possible to collectively detect whether or not dental plaque and dental calculus are present, but dental plaque and dental calculus cannot be distinguished from each other. Therefore, if a user is prompted to continue toothbrushing (brushing) based on the detection result that a biological deposit is present, the user will continue to brush his/her teeth even after dental plaque is already removed and only dental calculus remains. As a result, there is a risk that the user will brush his/her teeth excessively, and wounding the gums and causing bleeding therefrom or periodontal disease.

Accordingly, the present invention was achieved in order to provide a tooth brush with which it can be determined whether or not, regarding dental plaque and dental calculus, a state in which dental plaque is removed and only dental calculus remains has been brought about.

Also, the present invention was achieved in order to provide a system including such a toothbrush.

In order to solve the foregoing problem, a toothbrush of the present invention includes:

a main body including a head portion having a bristle raising surface on which bristles are provided in a standing manner;

a light emission unit configured to emit light through a specific region of the bristle raising surface to a tooth surface, and a light reception unit configured to receive radiated light from the tooth surface resulting from the light through the specific region, the light emission unit and the light reception unit being provided in the main body;

a detection unit configured to collectively detect whether or not dental plaque or dental calculus is present on the tooth surface based on an output from the light reception unit; and a determination unit configured to determine that dental calculus is present on the tooth surface when a state in which the detection unit detects the presence of dental plaque or dental calculus continues for a predetermined period from a start of brushing of the tooth surface.

Here, "collectively" detecting whether or not dental plaque or dental calculus is present means that "presence" is detected when at least one of dental plaque and dental calculus is present, and "absence" is detected when neither dental plaque nor dental calculus is present.

Moreover, the "predetermined period" after the start of brushing is set to be within a range of 3 to 5 seconds, for example, but there is no limitation thereto.

With the toothbrush of the present invention, the light emission unit emits light through the specific region of the bristle raising surface to the tooth surface. The light reception unit receives the radiated light from the tooth surface resulting from the light through the specific region. The detection unit collectively detects whether or not dental plaque or dental calculus is present on the tooth surface using the method disclosed in Patent Literature 1 (JP 2002-515276A), a patent application (Japanese Patent Application No. 2016-060012) that was previously proposed by the applicant of the present invention, or the like based on the output from the light reception unit. Furthermore, when the state in which the presence of dental plaque or dental calculus is detected by the detection unit continues for a predetermined period after the start of brushing of the tooth surface, the determination unit determines that dental calculus is present on the tooth surface. The reason for such determination is that, regarding dental plaque and dental calculus, a substance that cannot be removed by brushing is dental calculus, and therefore, it can be considered that only dental calculus remains when the state in which the presence of dental plaque or dental calculus is detected by the detection unit continues for a predetermined period after the start of brushing of the tooth surface. Accordingly, with this toothbrush, it can be determined whether or not, regarding dental plaque and dental calculus, a state in which dental plaque is removed and only dental calculus remains has been brought about. As a result, it is possible to reduce the risk that the user will brush his/her teeth excessively, wounding the gums and causing bleeding therefrom or periodontal disease.

It should be noted that, in the "specific region" of the bristle raising surface, it is desirable that the bristles are omitted.

With a toothbrush according to an embodiment, the detection unit and the determination unit are provided in the main body.

With the toothbrush according to this embodiment, the main body is provided with the detection unit and the determination unit. Therefore, using only the constituents provided in the main body, it is possible to determine whether or not, regarding dental plaque and dental calculus, a state in which dental plaque is removed and only dental calculus remains has been brought about. This makes it possible to omit an optical fiber, wire, or the like that extends from the toothbrush to an external device. In this kind of case, the user can easily brush his/her teeth without any hindrance when brushing his/her teeth using this toothbrush.

With a toothbrush according to an embodiment, a driving unit for vibrating, for brushing, the head portion together with the bristles is provided inside of the main body, and the toothbrush includes a control unit configured to perform control for reducing an intensity of vibration performed by the driving unit when the determination unit determines that dental calculus is present on the tooth surface.

With the toothbrush according to this embodiment, the control unit controls the driving unit to reduce the intensity of vibration caused by the driving unit when the determination unit determines that dental calculus is present on the tooth surface. Therefore, it is possible to further reduce the risk that the user will brush his/her teeth excessively.

A toothbrush according to an embodiment further includes a notification unit configured to perform notification of a state detected by the detection unit or a result of determination by the determination unit.

Here, the "notification" performed by the notification unit widely encompasses sounding of a buzzer sound, illumination or blinking of a lamp, display on a display screen, and the like.

With the toothbrush according to this embodiment, the notification unit performs notification of a state detected by the detection unit or a result of the determination by the determination unit. Therefore, the user can easily find out whether or not dental plaque or dental calculus is present on the tooth surface or that dental calculus is present on the tooth surface.

It should be noted that it is desirable to perform notification of the state detected by the detection unit and the result of the determination by the determination unit using different means. For example, when a lamp is turned on and off to perform notification whether or not dental plaque or dental calculus is present as a state detected by the detection unit, it is desirable to "sound a buzzer sound" to notify that "dental calculus is present" as the result of the determination by the determination unit. This makes it easy for the user to recognize a distinction between the notification of the state detected by the detection unit (dental plaque or dental calculus is present) and the notification of the result of the determination by the determination unit (dental calculus is present).

With a toothbrush according to an embodiment, when the determination unit determines that dental calculus is present on the tooth surface, or when the state detected by the detection unit shifts from a state in which dental plaque or dental calculus is present to a state in which neither dental plaque nor dental calculus is present, the notification unit performs notification for prompting a change of a brushing region brushed with the bristles in tooth rows.

Here, the "brushing region" refers to a region brushed with the bristles (a region with which the bristles are in contact) out of a plurality of regions that are defined by dividing the surfaces of the tooth rows in the oral cavity.

When the determination unit determines that dental calculus is present on the tooth surface while the user is brushing a certain brushing region, the user should finish brushing that brushing region and start brushing another region because the dental calculus cannot be removed even if the user further continues brushing that brushing region. Moreover, when the state detected by the detection unit shifts from a state in which dental plaque or dental calculus is present to a state in which neither dental plaque nor dental calculus is present while the user is brushing a certain brushing region, the user should finish brushing that brushing region and start brushing another region because neither dental plaque nor dental calculus is present in that brushing region. Therefore, with the toothbrush according to this embodiment, when the determination unit determines that dental calculus is present on the tooth surface, or when the state detected by the detection unit shifts from a state in which dental plaque or dental calculus is present to a state in which neither dental plaque nor dental calculus is present, the notification unit performs notification for prompting a change of the brushing region brushed with the bristles in the tooth rows. This notification prompts the user to finish brushing the current brushing region and start brushing another region, for example. Therefore, it is possible to further reduce the risk that the user will brush his/her teeth excessively.

A toothbrush according to an embodiment further includes:

a brushing region detection unit configured to detect a brushing region brushed with the bristles in tooth rows; and a storage unit in which data for each brushing region indicating whether or not the determination unit has determined that dental calculus is present on the tooth surface is stored.

With the toothbrush according to this embodiment, the brushing region detection unit detects the brushing region brushed with the bristles in the tooth rows. Data from each brushing region indicating whether or not the determination unit has determined that dental calculus is present on the tooth surface is stored in the storage unit. Therefore, the user can recognize in which region of the tooth rows in his/her oral cavity dental calculus remains by referring to the date stored in the storage unit.

A toothbrush according to an embodiment further includes a communication unit configured to be capable of transmitting the data stored in the storage unit to an external device from the main body.

With the toothbrush according to this embodiment, the communication unit can transmit the data stored in the storage unit to an external device from the main body. This makes it possible to apply the data stored in the storage unit of the toothbrush to various applications.

A system according to another aspect of the present invention includes the above-mentioned toothbrush and a computer apparatus provided outside of a main body of the toothbrush, wherein the computer apparatus includes:

a communication unit configured to be capable of receiving data from the storage unit of the toothbrush;

a display processing unit configured to process the data from the storage unit and produce an image showing a region of the tooth rows in which dental calculus is present; and a display unit on which the image produced by the display processing unit is displayed.

Here, it is sufficient that the "computer apparatus" is substantially a computer apparatus such as a smartphone or a tablet-type device irrespective of its name.

With the system of the present invention, the communication unit of the computer apparatus receives the data from the storage unit of the toothbrush. The display processing unit processes the data from the storage unit and produces an image showing a region of the tooth rows in which dental calculus is present. The image produced by the display processing unit is displayed on the display unit. When the user sees this image, he/she can intuitively recognize the region of his/her tooth rows in which dental calculus is present. Therefore, the user can appropriately determine whether or not he/she should have an examination and treatment from a dentist.

As is clear from the description above, with the toothbrush of the present invention, it is possible to determine whether or not, regarding dental plaque and dental calculus, a state in which dental plaque is removed and only dental calculus remains has been brought about.

In addition, with the system of the present invention, the user can intuitively recognize the region of his/her tooth rows in which dental calculus is present.

DETAILED DESCRIPTION

Figure 1B:
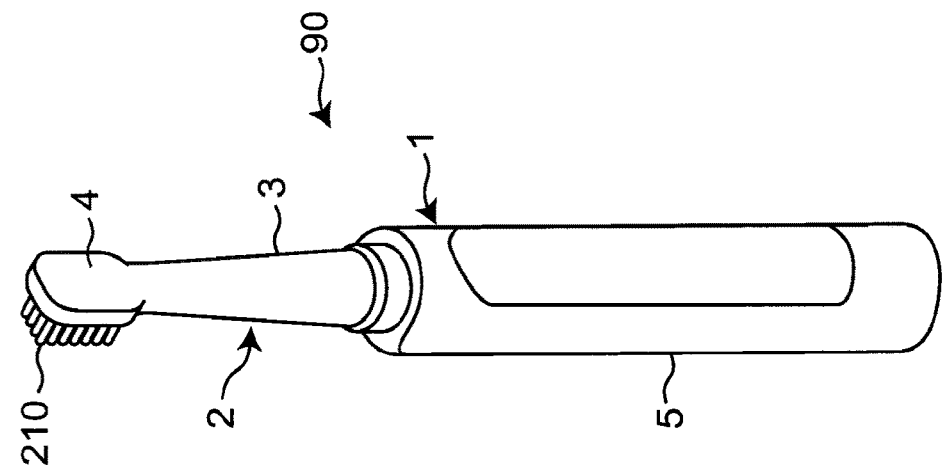
FIG. 1B is a perspective view of the exterior of an electric toothbrush of an embodiment of the present invention as viewed from mutually opposite sides.
Figure 1A:
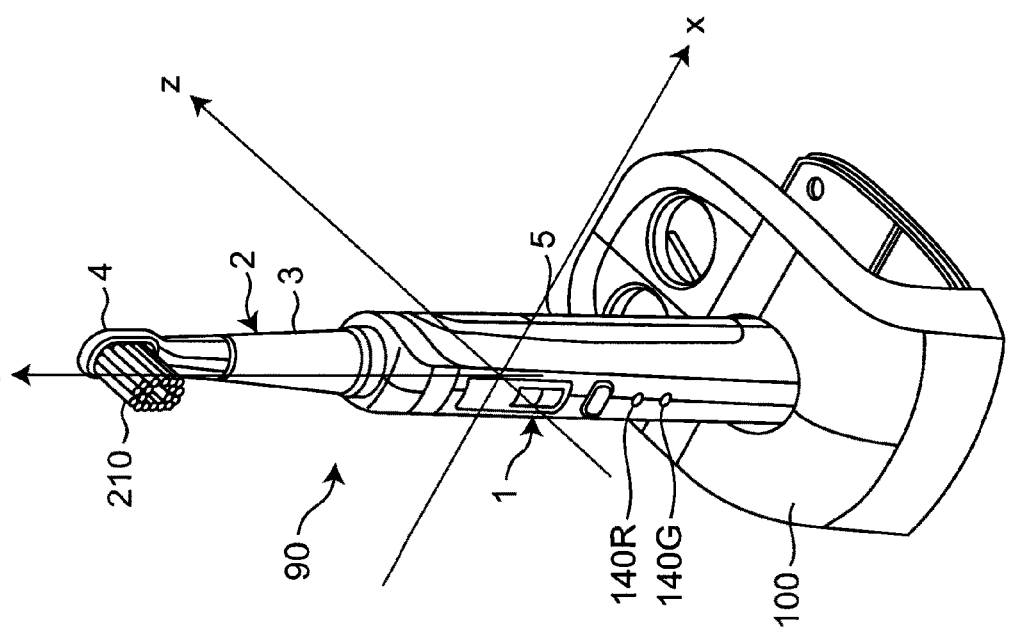
FIG. 1A is a perspective view of the exterior of an electric toothbrush of an embodiment of the present invention as viewed from mutually opposite sides.

Hereinafter, an embodiment of the present invention will be described in detail with reference to the drawings.
Configuration of Electric Toothbrush FIGS. 1A and 1B show perspective views of the exterior of an electric toothbrush (the entirety of which is denoted by reference numeral 90) of an embodiment, in which a dental plaque detection apparatus of the present invention is incorporated, as viewed from mutually opposite sides. The electric toothbrush 90 includes a head portion 4 on which bristles 210 are provided in a standing manner, a grip portion 5 that is to be gripped with a hand, and a neck portion 3 that couples the head portion 4 and the grip portion 5 together. The head portion 4 and the neck portion 3 integrally constitute a brush member 2, which can be attached to and detached from the grip portion 5. The head portion 4, the neck portion 3, and the grip portion 5 are collectively referred to as a main body 1. The main body 1 has a shape that is elongated in one direction for convenience of toothbrushing. It should be noted that a charger 100 is illustrated in FIG. 1A.

Figure 2A:
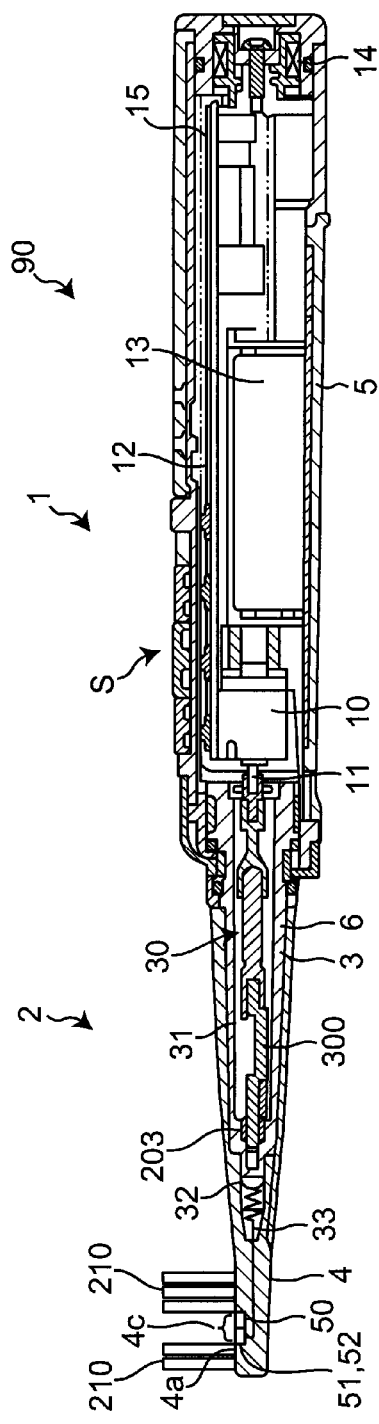
FIG. 2A is a vertical cross-sectional view of the electric toothbrush taken along a lengthwise direction.

FIG. 2A is a vertical cross-sectional view of the electric toothbrush 90 taken along a lengthwise direction. The grip portion 5 includes a stem 6 that is provided so as to protrude from the outer housing of the grip portion 5 toward the neck portion 3. The stem 6 has a cylindrical shape with a closed leading end. In this example, the neck portion 3 of the brush member 2 is attached and fitted so as to cover the stem 6. Since the brush member 2 is a consumable component, it can be attached to and detached from the grip portion 5 such that it can be replaced with a new one. In this example, the bristles (brush) 210 are provided in a standing manner on a surface (bristle raising surface) 4a on one side of the head portion 4 of the brush member 2, so as to protrude about 10 mm to 12 mm from the bristle raising surface 4a, through implantation in this example. It should be noted that the bristles 210 may be welded or adhered instead of being implanted.

A power switch S for switching power on and off is provided on the outer surface of the grip portion 5 of the main body 1. Also, a motor 10 serving as a driving source, a drive circuit 12, a rechargeable battery 13 serving as a power source unit, a coil 14 for charging, an acceleration sensor 15, and the like are provided inside of the grip portion 5. When the rechargeable battery 13 is to be charged, contactless charging can be performed through electromagnetic induction by merely placing the main body 1 on the charger 100 shown in FIG. 1A.

As shown in FIG. 2A, a bearing 203 is provided inside of the stem 6. The leading end of an eccentric shaft 30 coupled to a rotary shaft 11 of the motor 10 is inserted into the bearing 203. The eccentric shaft 30 has a weight 300 near the bearing 203, and the center of gravity of the eccentric shaft 30 is shifted from the rotary center. When the drive circuit 12 supplies a drive signal (e.g., a pulse width modulation signal) corresponding to the operation mode to the motor 10 and the rotary shaft 11 of the motor 10 is rotated, the eccentric shaft 30 also rotates accompanying the rotation of the rotary shaft 11. The eccentric shaft 30 performs the action of pivoting about the rotational center since its center of gravity is shifted from the rotational center. Accordingly, the leading end of the eccentric shaft 30 repeatedly collides with the inner surface of the bearing 203, causing the bristles 210 to vibrate (move) at a high speed.

In a specific region 4c in the approximate center of the bristle raising surface 4a of the head portion 4, the bristles are omitted. A light emission unit 50, a first light reception unit 51, and a second light reception unit 52 are arranged side by side inside of the head portion 4, corresponding to the specific region 4c. A portion (outer housing) of the bristle raising surface 4a of the head portion 4 that includes at least the specific region 4c is made of a transparent resin material with a thickness of about 1 mm to 3 mm.

Figure 2B:
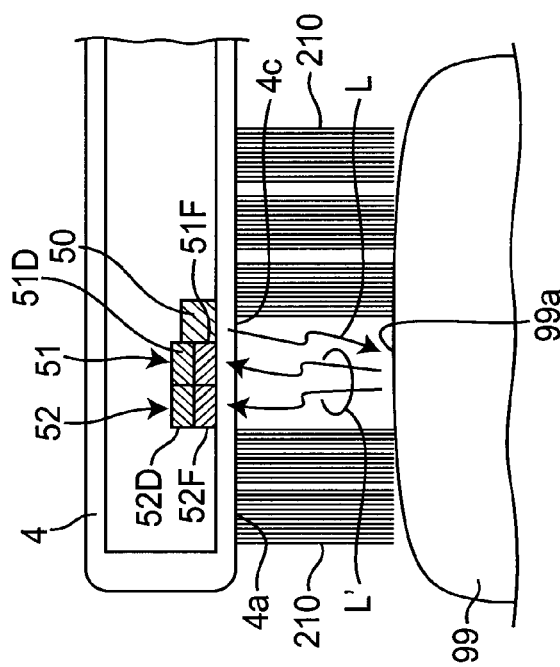
FIG. 2B is an enlarged view of a head portion during toothbrushing.

As shown in FIG. 2B, the light emission unit 50 includes a light emitting diode that emits excitation light L having a peak wavelength that corresponds to ultraviolet or blue to a tooth surface 99a through the specific region 4c. In this example, the light emitting diode is an LED (model number: SM0603UV-405) manufactured by Bivar Corp., and generates light L having a peak wavelength of 405 nm.

The first light reception unit 51 includes a first optical filter member 51F that receives radiated light L' from the tooth surface 99a through the specific region 4c and transmits only a spectral component in a first wavelength range in the radiated light L', and a first photodiode 51D that receives only the spectral component in the first wavelength range passing through the first optical filter member 51F. In this example, the first optical filter member 51F is a longpass filter (model number: LV0610) manufactured by Asahi Spectra Co., Ltd., and transmits light with wavelengths of 620 nm or more as the spectral component in the first wavelength range and blocks light with wavelengths of less than 620 nm (high-pass type). In this example, the first photodiode 51D is a PD (Photo Diode) (model number: NJL6401R-3) manufactured by New Japan Radio Co., Ltd.

The second light reception unit 52 includes a second optical filter member 52F that receives radiated light L' from the tooth surface 99a through the specific region 4c and transmits only a spectral component in a second wavelength range in the radiated light L', and a second photodiode 52D that receives only the spectral component in the second wavelength range passing through the second optical filter member 52F. In this example, the second optical filter member 52F is a longpass filter (model number: LV0550) manufactured by Asahi Spectra Co., Ltd., and transmits light with wavelengths of 550 nm or more as the spectral component in the second wavelength range and blocks light with wavelengths of less than 550 nm (high-pass type). In this example, as is the case with the first photodiode 51D, the second photodiode 52D is a PD (Photo Diode) (model number: NJL6401R-3) manufactured by New Japan Radio Co., Ltd.

It should be noted that the light emission unit 50, the first light reception unit 51, and the second light reception unit 52 are electrically connected to the drive circuit 12 via a lead wire 31, a contact terminal 32, and a spring-shaped terminal 33.

The first light reception unit 51 and the second light reception unit 52 need not be photodiodes and may be phototransistors. Moreover, the excitation light L from the light emission unit 50 and the radiated light L' from the tooth surface 99a may pass through different portions of the specific region 4c.

In this example, the acceleration sensor 15 shown in FIG. 2A is constituted by a multi-axis acceleration sensor (here, a three-axis acceleration sensor, namely an xyz-axis acceleration sensor). In this example, as shown in FIG. 1A, the x, y, and z axes are set such that the x axis is parallel with the brush surface (a plane formed of the leading ends of the bristles 210 that is parallel with the bristle raising surface 4a), the y axis corresponds to the lengthwise direction of the main body 1, and the z axis is orthogonal to the brush surface. That is, when the main body 1 is placed on the charger 100, the gravitational acceleration vector is parallel with the y axis; when the brush surface faces upward, the gravitational acceleration vector is parallel with the z axis; and when the main body 1 is oriented horizontally and the brush surface faces sideward, the gravitational acceleration vector is parallel with the x axis. The outputs from the respective axes of the acceleration sensor 15 are input into a control unit 110, which will be described later, and used in a known method (e.g., a method disclosed in JP 2011-139844A or JP 2013-42906A) in order to detect a brushing region (which will be described later).

A piezoresistance-type, capacitance-type, or heat detection-type MEMS (micro electro mechanical systems) sensor can be favorably used as the acceleration sensor 15. The reason for this is that an MEMS sensor is very small and is thus easily incorporated into the main body 1. However, the type of the acceleration sensor 15 is not limited thereto, and an electrodynamic sensor, a strain gauge-type sensor, a piezoelectric sensor, or the like may be used. In addition, although not particularly shown, it is preferable to provide correction circuits for correcting the balance of sensitivities, temperature characteristics of the sensitivities, temperature drift, and the like of the sensor regarding the respective axes. Moreover, a bandpass filter (low-pass filter) for removing dynamic acceleration components, noise, and the like may be provided. Furthermore, noise may be reduced by smoothing the waveforms of the outputs from the acceleration sensor.

Figure 3:
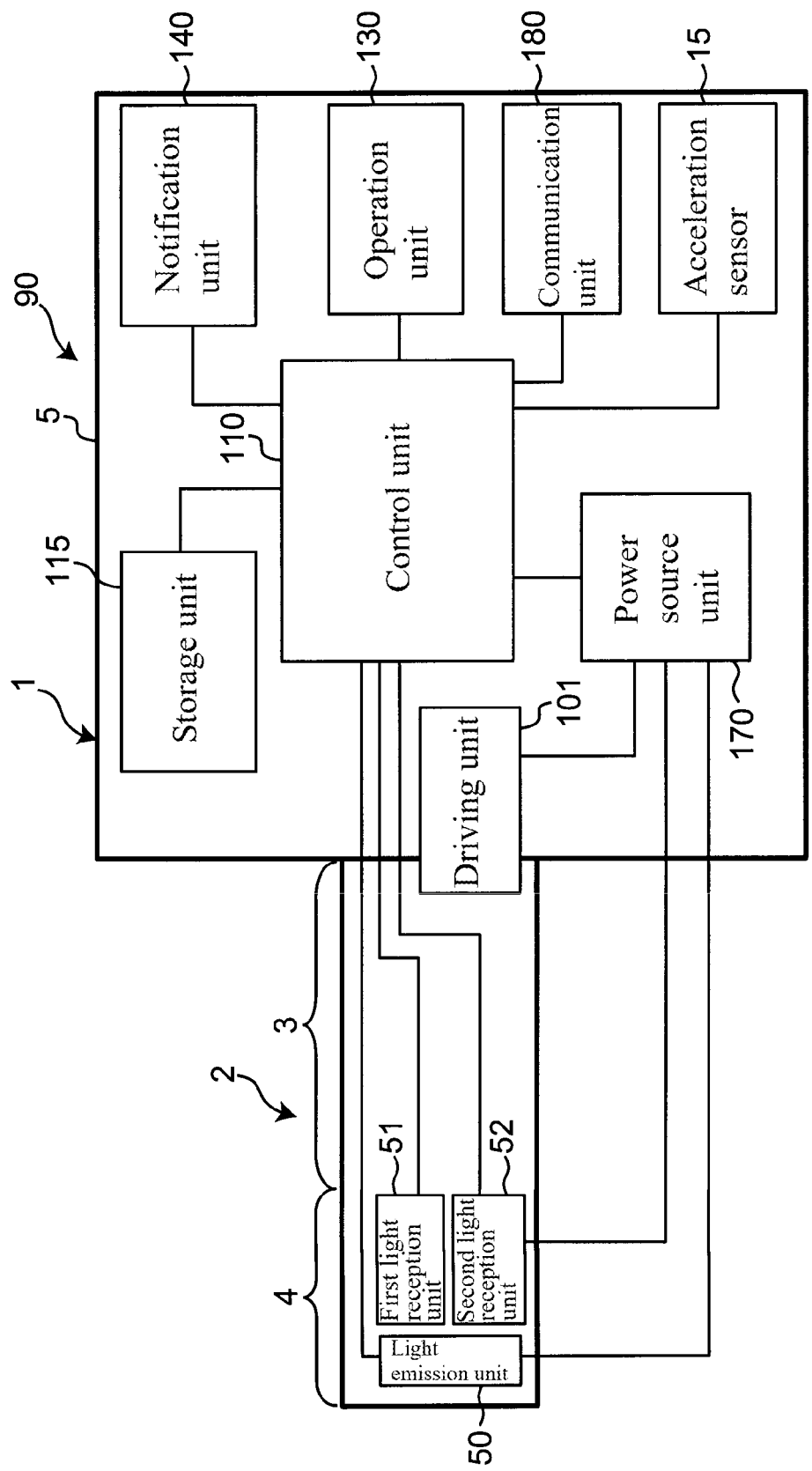
FIG. 3 is a diagram showing a block configuration of a control system of the electric toothbrush.

FIG. 3 shows a block configuration of a control system of the electric toothbrush 90. In addition to the acceleration sensor 15, a control unit 110, a storage unit 115, an operation unit 130, a notification unit 140, a communication unit 180, and a power source unit 170, which are included in the above-described drive circuit 12, are provided inside of the grip portion 5 of the electric toothbrush 90. It should be noted that the driving unit 101 indicates the above-described motor 10, rotary shaft 11, eccentric shaft 30, bearing 203, and weight 300.

The control unit 110 includes a CPU (central processing unit) that operates according to software, and executes driving of the motor 10, as well as processing for determining whether or not dental plaque or dental calculus is present on the tooth surface 99a, and other types of processing. In addition, the control unit 110 has a built-in timer that counts a time.

The operation unit 130 includes the above-described power switch S and functions so that the user switches on and off the power source of the electric toothbrush 90.

In this example, the storage unit 115 includes an EEPROM (electrically erasable read-only memory) that can non-temporarily store data. A control program for controlling the control unit 110 is stored in the storage unit 115. In addition, in this example, data (referred to as "dental plaque/dental calculus data") on whether or not dental plaque and/or dental calculus is present in each region of the tooth rows is stored as a table in the storage unit 115 (this will be described later).

In this example, the notification unit 140 includes a red LED lamp 140R and a green LED lamp 140G (see FIG. 1A), and performs notification about whether or not dental plaque or dental calculus is present by turning the LED lamps 140R and 140G on and off. Furthermore, a configuration may be employed in which the notification unit 140 further includes a buzzer (not shown) and performs notification about whether or not dental plaque or dental calculus is present by sounding a buzzer sound. Instead or in addition, notification about whether or not dental plaque or dental calculus is present may be performed by switching the vibration of the motor 10 between a strong level and a weak level.

The communication unit 180 is controlled by the control unit 110 so as to transmit predetermined information to an external device via a network, or serves as an input unit so as to receive information from an external device via a network and transfers the information to the control unit 110. In this example, this communication via a network is wireless communication (e.g, BT (Bluetooth (registered trademark) communication or BLE (Bluetooth (registered trademark) low energy) communication). The network is typically a household LAN (local area network) or in-hospital LAN, but there is no limitation thereto, and the network may also be the Internet or the like.

The power source unit 170 includes the above-described rechargeable battery 13, and supplies power (DC 2.4 V in this example) to the units in this electric toothbrush 90.

First Operational Example

Figure 4:
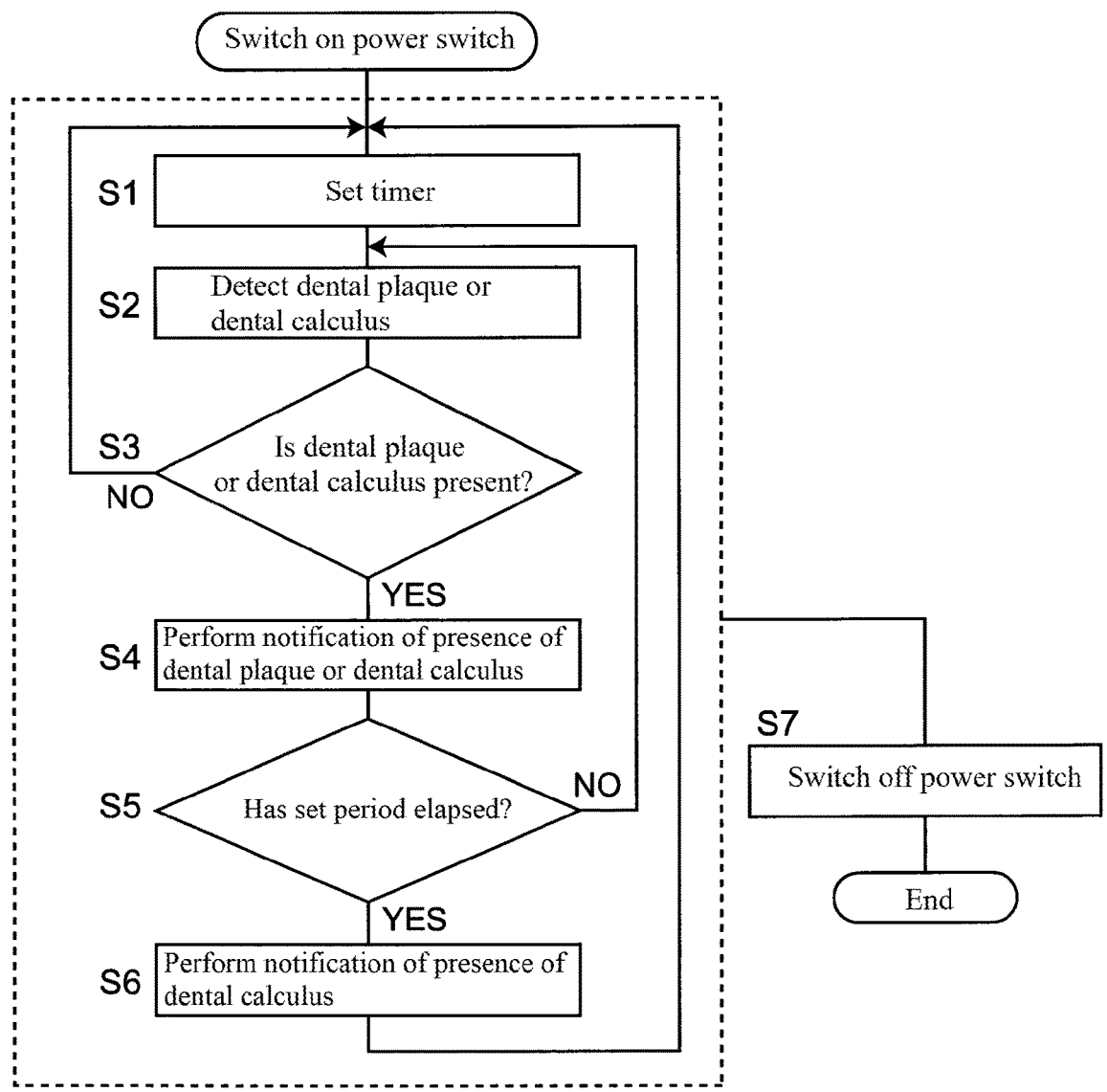
FIG. 4 is a flowchart illustrating a first operational example of the electric toothbrush.

FIG. 4 shows an example of a flow of a process, performed by the control unit 110 of the electric toothbrush 90, for determining whether or not dental plaque and/or dental calculus is present on the tooth surface 99a. With the electric toothbrush 90, when the user switches on the power switch S, the control unit 110 causes the bristles 210 to vibrate by rotating the motor 10.

When the power switch S is switched on, in step S1 shown in FIG. 4, the control unit 110 sets a timer that counts a predetermined period Δt after the start of brushing of the tooth surface 99a. The set period Δt set in this timer is a period for determining whether or not, regarding dental plaque and dental calculus, only dental calculus remains on the tooth surface 99a (this will be described later). In this example, the set period Δt is set to be within a range of 3 seconds to 5 seconds for the purpose of preventing the user from brushing his/her teeth excessively.

Subsequently, in step S2 shown in FIG. 4, the control unit 110 serves as a detection unit and collectively detects whether or not dental plaque or dental calculus is present on the tooth surface 99a using the method disclosed in a patent application (Japanese Patent Application No. 2016-060012) that was previously proposed by the applicant of the present invention.

Specifically, as shown in FIG. 2B, the light emission unit 50 is turned on, and the excitation light L is emitted from the light emission unit 50 to the tooth surface 99a through the specific region 4c. In response, the radiated light L' is radiated from the tooth surface 99a. The radiated light L' passes through the specific region 4c and is received by the first reception unit 51 and the second light reception unit 52. The output from the first light reception unit 51 and the output from the second light reception unit 52 are input into the control unit 110 as a first output value OUT1 and a second output value OUT2, respectively.

Subsequently, the control unit 110 serves as a zero point correction unit and performs a correction in which components (i.e., a first output value OUT1b and a second output value OUT2b that are values when the light emission unit 50 is off) of ambient light Lb around the tooth surface 99a are subtracted from the first output value OUT1 and the second output value OUT2. Specifically, differences, namely a first output value ΔOUT1 and a second output value ΔOUT2, are calculated as corrected values in accordance with the following calculations:

$$\Delta OUT1 = OUT1 - OUT1b, \text{ and}$$

$$\Delta OUT2 = OUT2 - OUT2b.$$

Figure 6A:
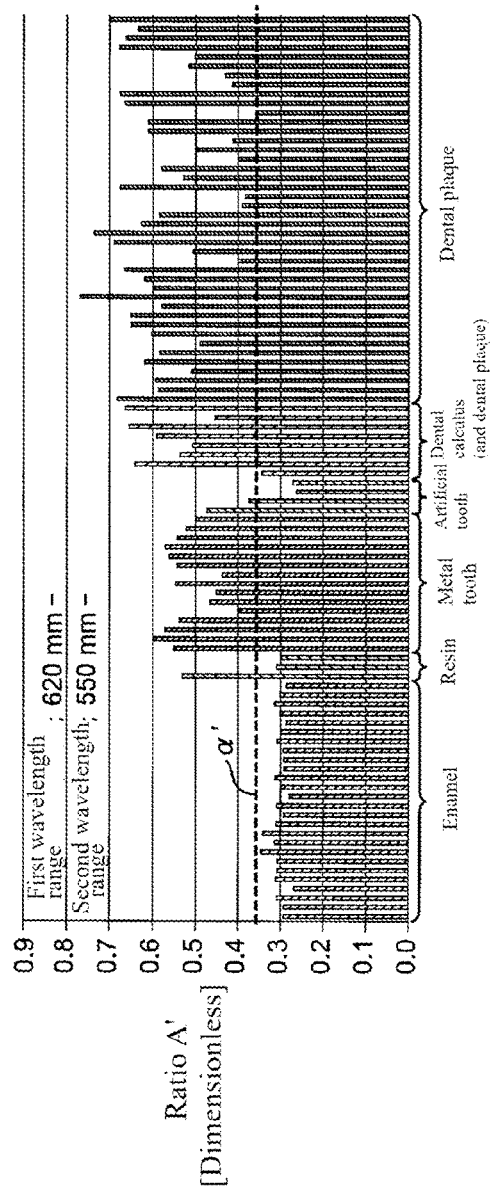
FIG. 6A is a diagram showing ratios A' between a first output value ΔOUT1 and a second output value ΔOUT2 for enamel, resin, a metal tooth, an artificial tooth (ceramic or plastic), dental calculus, and dental plaque.

Here, FIG. 6A shows ratios A' between the first output value ΔOUT1 and the second output value ΔOUT2. It should be noted that, in this example, the ratio A' is defined as the following equation:

$$A' = \Delta OUT1/\Delta OUT2.$$

Figure 6B:
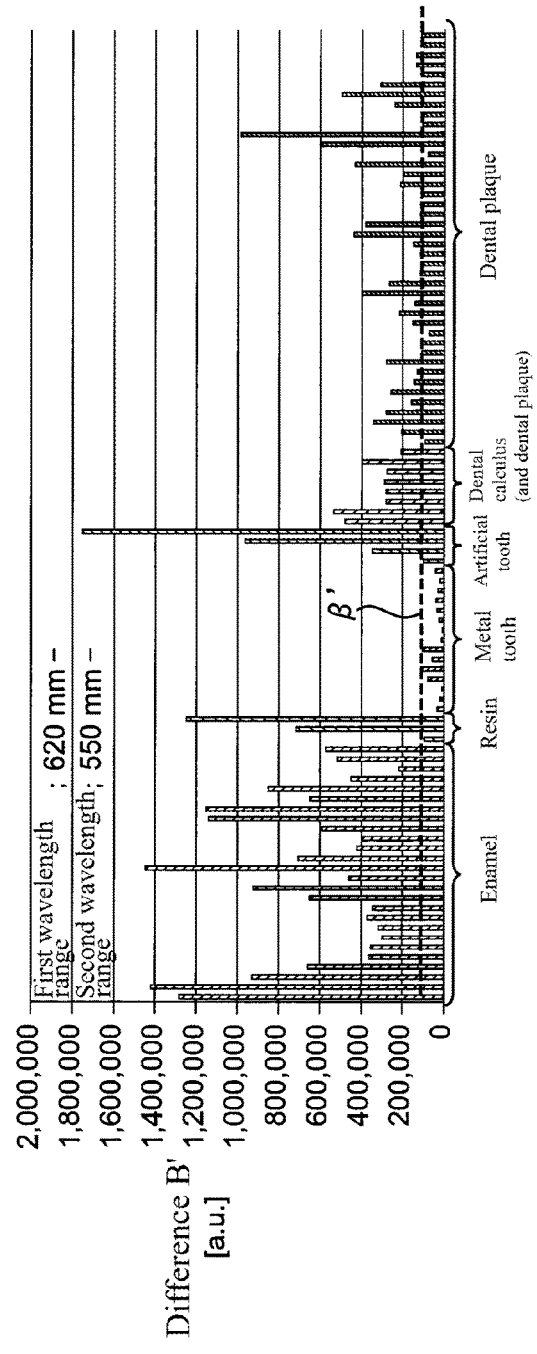
FIG. 6B is a diagram showing differences B' between the second output value ΔOUT2 and the first output value ΔOUT1 for enamel, resin, a metal tooth, an artificial tooth (ceramic or plastic), dental calculus, and dental plaque.

In FIG. 6A and FIG. 6B, which will be described later, respective bars that are laterally aligned correspond to an enamel sample, a resin sample, a metal tooth sample, an artificial tooth sample (ceramic or plastic), a dental calculus sample, and a dental plaque sample. As is clear from FIG. 6A, regarding the group consisting of enamel, resin, and an artificial tooth (ceramic or plastic), the ratios A' are smaller than about 0.35. On the other hand, regarding the group consisting of a metal tooth, dental calculus, and dental plaque, the ratios A' are larger than about 0.35. Therefore, determining whether or not the ratio A' is larger than a first threshold value α'=0.35 makes it possible to identify the group consisting of enamel, resin, and an artificial tooth (ceramic or plastic) and the group consisting of a metal tooth, dental calculus, and dental plaque as separate groups.

Similarly, FIG. 6B shows differences B' between the first output value ΔOUT1 and the second output value ΔOUT2. It should be noted that, in this example, the difference B' is defined as the following equation:

$$B' = \Delta OUT2 - \Delta OUT1.$$

As is clear from FIG. 6B, regarding the group consisting of a metal tooth, the difference B' is smaller than about 100,000 (a.u.). On the other hand, regarding the group consisting of enamel, resin, an artificial tooth (ceramic or plastic), dental calculus, and dental plaque, the difference B' is larger than about 100,000 (a.u.). Therefore, determining whether or not the difference B' is larger than a second threshold value β'=100,000 (a.u.) makes it possible to identify the group consisting of a metal tooth and the group consisting of enamel, resin, an artificial tooth (ceramic or plastic), dental calculus, and dental plaque as separate groups.

As described above, a combination of the result obtained by determining whether or not the ratio A' shown in FIG. 6A is larger than the first threshold value α' and the result obtained by determining whether or not the difference B' shown in FIG. 6B is larger than the second threshold value β' is used to determine whether or not a substance present on the tooth surface 99a is dental plaque or dental calculus.

It should be noted that dental plaque turns into dental calculus when it gradually alters and deposits on a tooth surface, and therefore, it is difficult to physically distinguish dental plaque from dental calculus completely. This is the reason for the description "dental calculus (and dental plaque)" in FIGS. 6A and 6B.

As described above, the control unit 110 collectively detects whether or not dental plaque or dental calculus is present. That is, "presence" is detected when at least one of dental plaque and dental calculus is present, and "absence" is detected when neither dental plaque nor dental calculus is present.

Here, if it is determined that dental plaque or dental calculus is present (YES in step S3 shown in FIG. 4), the process moves to step S4, and the control unit 110 performs notification of the presence of dental plaque or dental calculus through momentary illumination (e.g., for 0.3 seconds; the same applies hereinafter) of the red LED lamp 140R by the notification unit 140, for example.

Next, in step S5 shown in FIG. 4, the control unit 110 determines whether or not the set period Δt set in the timer has elapsed. If the set period Δt has not elapsed (NO in step S5 shown in FIG. 4), the processing in steps S2 to S5 is repeated.

Thereafter, if the set period Δt set in the timer has elapsed while the state in which the presence of dental plaque or dental calculus is detected (YES in step S3 shown in FIG. 4) is maintained in step S3 shown in FIG. 4 (YES in step S5 shown in FIG. 4), the control unit 110 serves as a determination unit and determines that dental calculus is present on the tooth surface 99a.

The reason for such determination is that, as described above, regarding dental plaque and dental calculus, a substance that cannot be removed by brushing is dental calculus, and therefore, it can be considered that only dental calculus remains when the state in which the presence of dental plaque or dental calculus is detected continues for the set period Δt after the start of brushing of the tooth surface 99a. Therefore, with the electric toothbrush 90, it can be determined whether or not a state in which, regarding dental plaque and dental calculus, dental plaque is removed and only dental calculus remains has been brought about.

Subsequently, in step S6 shown in FIG. 4, the control unit 110 performs notification of the presence of dental calculus through momentary sounding of a buzzer sound by the notification unit 140, for example. As described above, in this example, the notification of the presence of dental calculus (step S6 shown in FIG. 4) is performed using a means different from that used for the notification of the presence of dental plaque or dental calculus (step S4 shown in FIG. 4). This makes it easy for the user to recognize a distinction between the notification of the presence of dental plaque or dental calculus and the notification of the presence of dental calculus. As a result, it is possible to reduce the risk that the user will brush his/her teeth excessively, wounding the gums and causing bleeding therefrom or periodontal disease.

On the other hand, if it is determined that neither dental plaque nor dental calculus is present (NO in step S3 shown in FIG. 4), the control unit 110 performs notification of the absence of both dental plaque and dental calculus through momentary illumination of the green LED lamp 140G by the notification unit 140, and then repeats the processing in steps S1 and S2 shown in FIG. 4. When the user switches off the power switch S in step S7 shown in FIG. 4, the control unit 110 finishes the process.

With the electric toothbrush 90, the grip portion 5 of the main body 1 is provided with the control unit 110 serving as a detection unit and a determination unit. Therefore, using only the constituents provided in the main body, it is possible to determine whether or not, regarding dental plaque and dental calculus, a state in which dental plaque is removed and only dental calculus remains has been brought about. This makes it possible to omit an optical fiber, wire, or the like that extends from the electric toothbrush 90 to an external device. Accordingly, the user can easily brush his/her teeth without any hindrance when brushing his/her teeth using the electric toothbrush 90.

Second Operational Example

The manner in which dental plaque and dental calculus adhere to a tooth depends on the type of the tooth (in the maxilla/mandible, molar/incisor, and so on) and the region of the tooth (the lingual side/buccal side, the side surface/occlusal surface of the tooth, and so on). Therefore, it is desirable to detect whether or not dental plaque and/or dental calculus is present on a region-by-region basis in the tooth rows.

Figure 7:
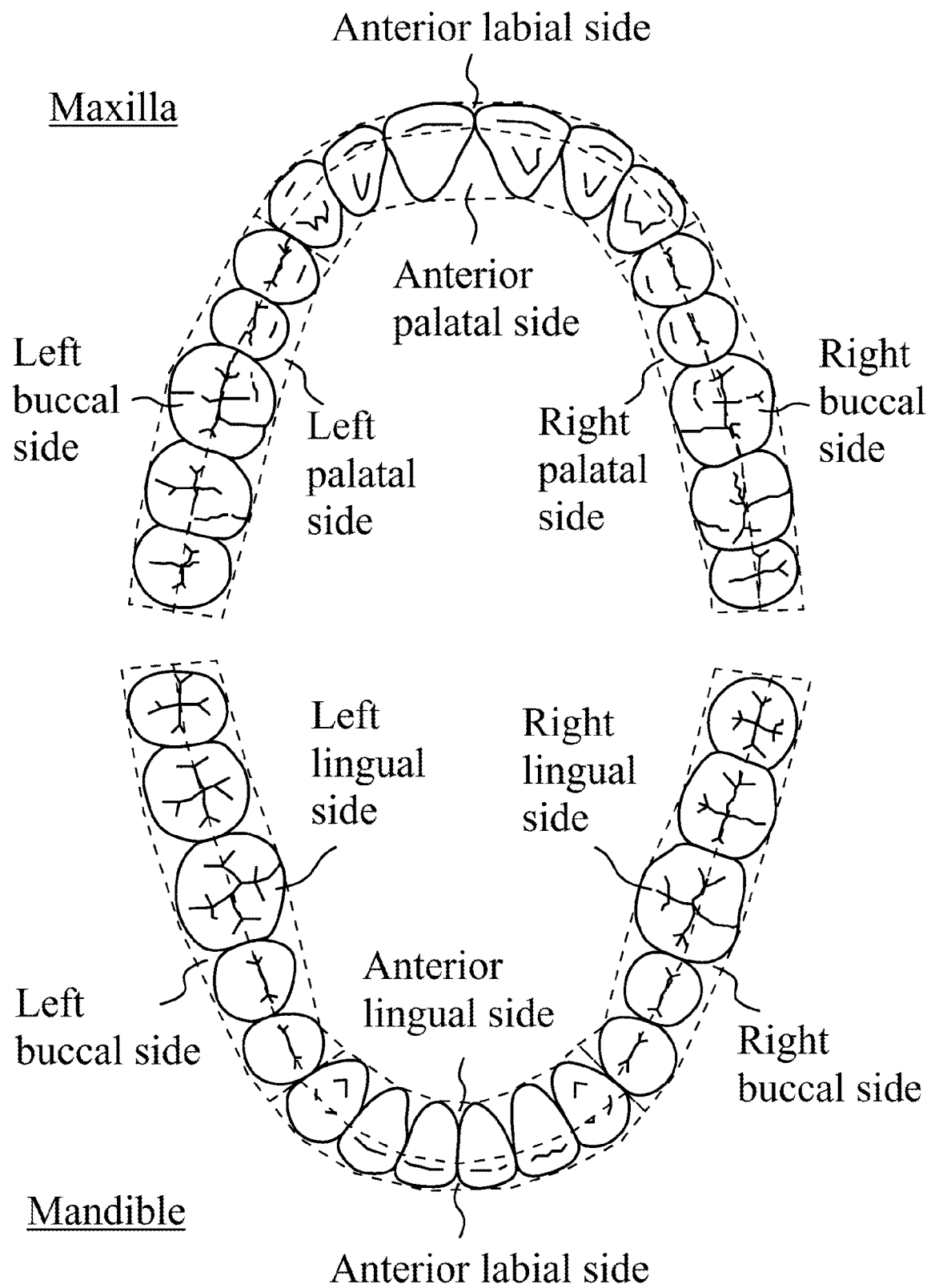
FIG. 7 is a diagram showing twelve regions of tooth rows in an oral cavity.

In this example, as shown in FIG. 7, the upper tooth row and lower tooth row are segmented into 12 regions: a maxillary anterior labial side; a maxillary anterior palatal side; a maxillary left buccal side; a maxillary left palatal side; a maxillary right buccal side; a maxillary right palatal side; a mandibular anterior labial side; a mandibular anterior lingual side; a mandibular left buccal side; a mandibular left lingual side; a mandibular right buccal side; and a mandibular right lingual side. However, the segmentation of the tooth rows is not limited thereto, and narrower segmentation may be carried out instead. For example, the tooth rows may be segmented based on the individual teeth, each tooth may be segmented into a left half section and a right half section, or the tooth rows may be segmented into left and right occlusal surfaces on the upper and lower sides.

Figure 5:
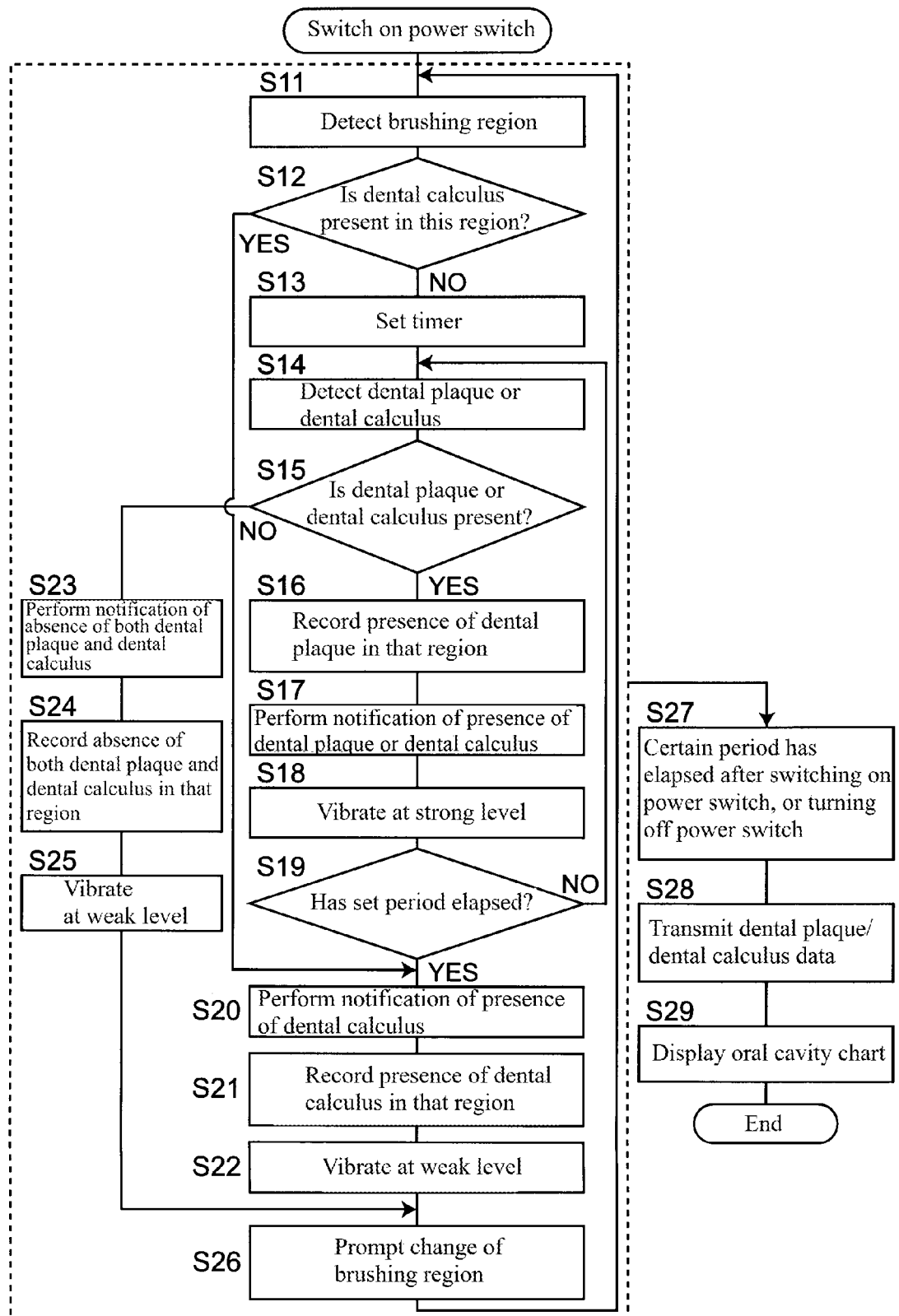
FIG. 5 is a flowchart illustrating a second operational example of the electric toothbrush.

FIG. 5 shows an example of a flow of a process, performed by the control unit 110 of the electric toothbrush 90, for determining whether or not dental plaque and/or dental calculus is present in each of such regions of the tooth rows. With the electric toothbrush 90, when the user switches on the power switch S, the control unit 110 causes the bristles 210 to vibrate by rotating the motor 10. In this example, the intensity of the vibration of the motor 10 is set to a weak level at first.

When the power switch S is switched on, in step S11 shown in FIG. 5, the control unit 110 serves as a brushing region detection unit and detects a region (referred to as "brushing region") that is currently being brushed with the bristles 210 of the head portion 4 (a region with which the bristles 210 are in contact) among the 12 regions of the tooth rows.

Specifically, the control unit 110 detects the current brushing region based on the outputs from the respective axes of the acceleration sensor 15 using a known method (e.g., a method disclosed in JP 2011-139844A or JP 2013-42906A). It should be noted that it is desirable to provide a load sensor for detecting brush pressure (load applied to the bristles 210) inside of the main body 1 to detect whether or not the bristles 210 are in contact with the brushing region.

Next, in step S12 shown in FIG. 5, the control unit 110 refers to the table of the dental plaque/dental calculus data set in the storage unit 115, and thus determines whether or not information on the presence or absence of dental calculus in the current brushing region has been already recorded. At the start of one instance of toothbrushing (referring to an operation performed for a certain period of time such as 3 minutes at most by the user), the dental plaque/dental calculus data of each of the regions has not yet been recorded (NO in step S12 shown in FIG. 5).

Table 1 below shows an example of the table of the dental plaque/dental calculus data set in the storage unit 115 at the start of toothbrushing (10:00 PM on 1 Jul. 2016 in this example).

TABLE 1

Table of dental plaque/dental calculus data (at start of toothbrushing)

| Region | Date and Time 2016 Jul. 1/22:00 |
| --- | --- |
| Maxillary anterior labial side | — |
| Maxillary anterior palatal side | — |
| Maxillary left buccal side | — |
| Maxillary left palatal side | — |
| Maxillary right buccal side | — |
| Maxillary right palatal side | — |
| Mandibular anterior labial side | — |
| Mandibular anterior lingual side | — |
| Mandibular left buccal side | — |
| Mandibular left lingual side | — |
| Mandibular right buccal side | — |
| Mandibular right lingual side | — |

The 12 regions of the tooth rows of the user are distinguishably listed in the table side (left column) of Table 1. The date and time when the dental plaque/dental calculus data is obtained is recorded in the table head (top of the right column) of Table 1. The information indicating whether or not dental plaque or dental calculus is present in each of the regions of the tooth rows is recorded in the table body (right column) of Table 1. A symbol "-" in Table 1 shows that the data has not yet been recorded.

Next, in step S13 shown in FIG. 5, the control unit 110 sets a timer that counts a predetermined period $\Delta t$ after the start of brushing of the tooth surface 99a. The set period $\Delta t$ set in this timer is a period for determining whether or not, regarding dental plaque and dental calculus, only dental calculus remains on the tooth surface 99*a* in the brushing region (this will be described later). In this example, the set period Δt is set to be within a range of 3 seconds to 5 seconds for the purpose of preventing the user from brushing his/her teeth excessively.

Subsequently, in step S14 shown in FIG. 5, the control unit 110 serves as a detection unit and collectively detects whether or not dental plaque or dental calculus is present on the tooth surface 99*a* using the method disclosed in a patent application (Japanese Patent Application No. 2016-060012) that was previously proposed by the applicant of the present invention. Specifically, the same processing as that in step S2 shown in FIG. 4, which has been described in detail above, is performed to collectively detect whether or not dental plaque or dental calculus is present.

Here, when the detection result (detection state) indicates that neither dental plaque nor dental calculus is present (NO in step S15 shown in FIG. 5), the process moves to step S23 shown in FIG. 5, and the control unit 110 performs notification of the absence of both dental plaque and dental calculus through momentary illumination of the green LED lamp 140G by the notification unit 140, for example.

Subsequently, in step S24 shown in FIG. 5, the control unit 110 records "absence" of both dental plaque and dental calculus in the brushing region in the table of the "dental plaque/dental calculus data" set in the storage unit 115. Furthermore, in step S25 shown in FIG. 5, the control unit 110 maintains the intensity of the vibration of the motor 10 at a weak level.

On the other hand, when the detection result (detection state) indicates that dental plaque or dental calculus is present (YES in step S15 shown in FIG. 5), the process moves to step S16 shown in FIG. 5, and the control unit 110 records "presence of dental plaque" in the brushing region in the table of the "dental plaque/dental calculus data" set in the storage unit 115. This record of "presence of dental plaque" indicates that dental plaque or dental calculus is present in the brushing region in practice.

Subsequently, in step S17 shown in FIG. 5, the control unit 110 performs notification of the presence of dental plaque or dental calculus through momentary illumination of the red LED lamp 140R by the notification unit 140, for example. Furthermore, in step S18 shown in FIG. 5, the control unit 110 switches the intensity of the vibration of the motor 10 from a weak level to a strong level such that dental plaque or dental calculus is easily removed.

Next, in step S19 shown in FIG. 5, the control unit 110 determines whether or not the set period Δt set in the timer has elapsed from the start of brushing of the brushing region. If the set period Δt has not elapsed (NO in step S19 shown in FIG. 5), the processing in steps S14 to S19 is repeated.

Thereafter, if the set period Δt set in the timer has elapsed while the state in which the presence of dental plaque or dental calculus is detected (YES in step S15 shown in FIG. 5) is maintained in step S15 shown in FIG. 5 (YES in step S19 shown in FIG. 5), the control unit 110 serves as a determination unit and determines that dental calculus is present on the tooth surface 99*a*.

The reason for such determination is that, as described above, regarding dental plaque and dental calculus, a substance that cannot be removed by brushing is dental calculus, and therefore, it can be considered that only dental calculus remains when the state (YES in step S15 shown in FIG. 5) in which the presence of dental plaque or dental calculus is detected continues for the set period Δt after the start of brushing of the brushing region. Therefore, with the electric toothbrush 90, it can be determined whether or not a state in which, regarding dental plaque and dental calculus, dental plaque is removed and only dental calculus remains has been brought about.

Subsequently, in step S20 shown in FIG. 5, the control unit 110 performs notification of the presence of dental calculus through momentary sounding of a buzzer sound, for example, instead of the illumination of the LED lamp by the notification unit 140. In this example, in the same manner as in the previous example, the notification of the presence of dental calculus (step S20 shown in FIG. 5) is performed using a means different from that used for the notification of the presence of dental plaque or dental calculus (step S17 shown in FIG. 5). This makes it easy for the user to recognize a distinction between the notification of the presence of dental plaque or dental calculus and the notification of the presence of dental calculus. As a result, it is possible to reduce the risk that the user will brush his/her teeth excessively, wounding the gums and causing bleeding therefrom or periodontal disease.

Subsequently, the process moves to step S21 shown in FIG. 5, and the control unit 110 rewrites the record from "presence of dental plaque" in the brushing region to "presence of dental calculus" in the table of the "dental plaque/dental calculus data" set in the storage unit 115. Furthermore, in step S22 shown in FIG. 5, the control unit 110 switches the intensity of the vibration of the motor 10 from a strong level to a weak level. This makes it possible to further reduce the risk that the user will brush his/her teeth excessively.

It should be noted that switching of the intensity of the vibration of the motor 10 (step S22 shown in FIG. 5) may be used instead of the notification of the presence of dental calculus (step S20 shown in FIG. 5) and step S20 may be omitted.

When the detection result (detection state) shifts from the presence of dental plaque or dental calculus to the absence of both dental plaque and dental calculus within the set period Δt set in the timer in step S15 shown in FIG. 5 (when step S15 shown in FIG. 5 shifts from YES to NO), the process moves to step S23 shown in FIG. 5, and the control unit 110 performs notification of the absence of both dental plaque and dental calculus through momentary illumination of the green LED lamp 140G by the notification unit 140, for example.

Here, the shift of the detection result (detection state) from the presence of dental plaque or dental calculus to the absence of both dental plaque and dental calculus means that dental plaque or dental calculus was present on the tooth surface 99*a* in the brushing region, but the substance (dental plaque or dental calculus) was removed through brushing, that is, the substance was dental plaque out of dental plaque and dental calculus.

Subsequently, in step S24 shown in FIG. 5, the control unit 110 rewrites the record from "presence of dental plaque" in the brushing region to "absence of both dental plaque and dental calculus" in the table of the "dental plaque/dental calculus data" set in the storage unit 115. Furthermore, in step S25 shown in FIG. 5, the control unit 110 switches the intensity of the vibration of the motor 10 from a strong level to a weak level. This makes it possible to further reduce the risk that the user will brush his/her teeth excessively.

As described above, any of "presence of dental plaque", "presence of dental calculus", or "absence of both dental plaque and dental calculus" in the current brushing region is recorded in the table of the dental plaque/dental calculus data set in the storage unit 115 (steps S16, S21, and S24 shown in FIG. 5).

If it is determined that dental calculus is present on the tooth surface 99a while the user is brushing a certain brushing region (YES in step S19 shown in FIG. 5), the user should finish brushing that brushing region and start brushing another region because the dental calculus cannot be removed even if the user further continues brushing that brushing region. Moreover, when the detection state shifts from the state in which dental plaque or dental calculus is present to the state in which neither dental plaque nor dental calculus is present (when step S15 shown in FIG. 5 shifts from YES to NO) while the user is brushing a certain brushing region, the user should finish brushing that brushing region and start brushing another region because neither dental plaque nor dental calculus is present in that brushing region. Therefore, after step S22 or step S25 shown in FIG. 5, the process moves to step S26, and the control unit 110 performs notification for prompting a change of the brushing region through momentary sounding of a buzzer sound by the notification unit 140, for example.

This notification prompts the user to finish brushing the current brushing region and start brushing another region, for example. Therefore, it is possible to further reduce the risk that the user will brush his/her teeth excessively.

It should be noted that notification for prompting a change of the brushing region (step S26 shown in FIG. 5) may be used instead of the notification of the presence of dental calculus (step S20 shown in FIG. 5) and step S20 may be omitted.

When the user moves the bristles 210 of the head portion 4 to another region, the process returns to step S11 shown in FIG. 5, and the control unit 110 serves as a brushing region detection unit again and detects a brushing region that is currently being brushed with the bristles 210 of the head portion 4. Then, the processing in steps S12 to S26 is repeated.

It should be noted that when the user moves the bristles 210 of the head portion 4 to the region whose state has been already recorded as "presence of dental calculus" in the table of the dental plaque/dental calculus data set in the storage unit 115 (YES in step S12 shown in FIG. 5), it is not necessary to detect again whether or not dental plaque or dental calculus is present. Therefore, the process moves to step S20 shown in FIG. 5, and the control unit 110 performs notification of the presence of dental calculus in the brushing region through momentary sounding of a buzzer sound by the notification unit 140, for example, (step S20 shown in FIG. 5), maintains the record of "presence of dental calculus" in the table of the dental plaque/dental calculus data (step S21 shown in FIG. 5), and maintains the intensity of the vibration of the motor 10 at a weak level (step S22 shown in FIG. 5). Then, the control unit 110 performs notification for prompting a change of the brushing region through momentary sounding of a buzzer sound by the notification unit 140, for example, (step S26 shown in FIG. 5).

In step S27 shown in FIG. 5, if a certain period (3 minutes in this example) has elapsed since the user switched on the power switch S, or the user switches off the power switch S, the control unit 110 finishes the process.

In such a case, the table of the dental plaque/dental calculus data shown as an example in Table 2 below is obtained in the storage unit 115 at the end of toothbrushing (10:02 PM on 1 Jul. 2016 in this example).

TABLE 2

Table of dental plaque/dental calculus data (at end of toothbrushing)

| Region | Date and Time 2016 Jul. 1/22:02 |
|---|---|
| Maxillary anterior labial side | None |
| Maxillary anterior palatal side | None |
| Maxillary left buccal side | None |
| Maxillary left palatal side | None |
| Maxillary right buccal side | Dental calculus |
| Maxillary right palatal side | None |
| Mandibular anterior labial side | None |
| Mandibular anterior lingual side | Dental calculus |
| Mandibular left buccal side | None |
| Mandibular left lingual side | None |
| Mandibular right buccal side | None |
| Mandibular right lingual side | None |

Referring to the table of the dental plaque/dental calculus data in Table 2, the user can recognize that dental calculus remains in two regions, namely "maxillary right buccal side" and "mandibular anterior lingual side" as shown in FIG. 7, in the tooth rows in his/her oral cavity, for example. It is found that neither dental plaque nor dental calculus is present in the regions other than the two regions. Also, it is found that no regions in which "dental plaque is present" remain at the end of toothbrushing.

The dental plaque/dental calculus data shown in Table 2 may be transmitted to an external computer apparatus such as a user's smartphone 600 (see FIG. 8) via a network due to the control unit 110 controlling the communication unit 180 (step S28 shown in FIG. 5). This makes it possible to use the dental plaque/dental calculus data in various applications.

System Configuration

Figure 8:
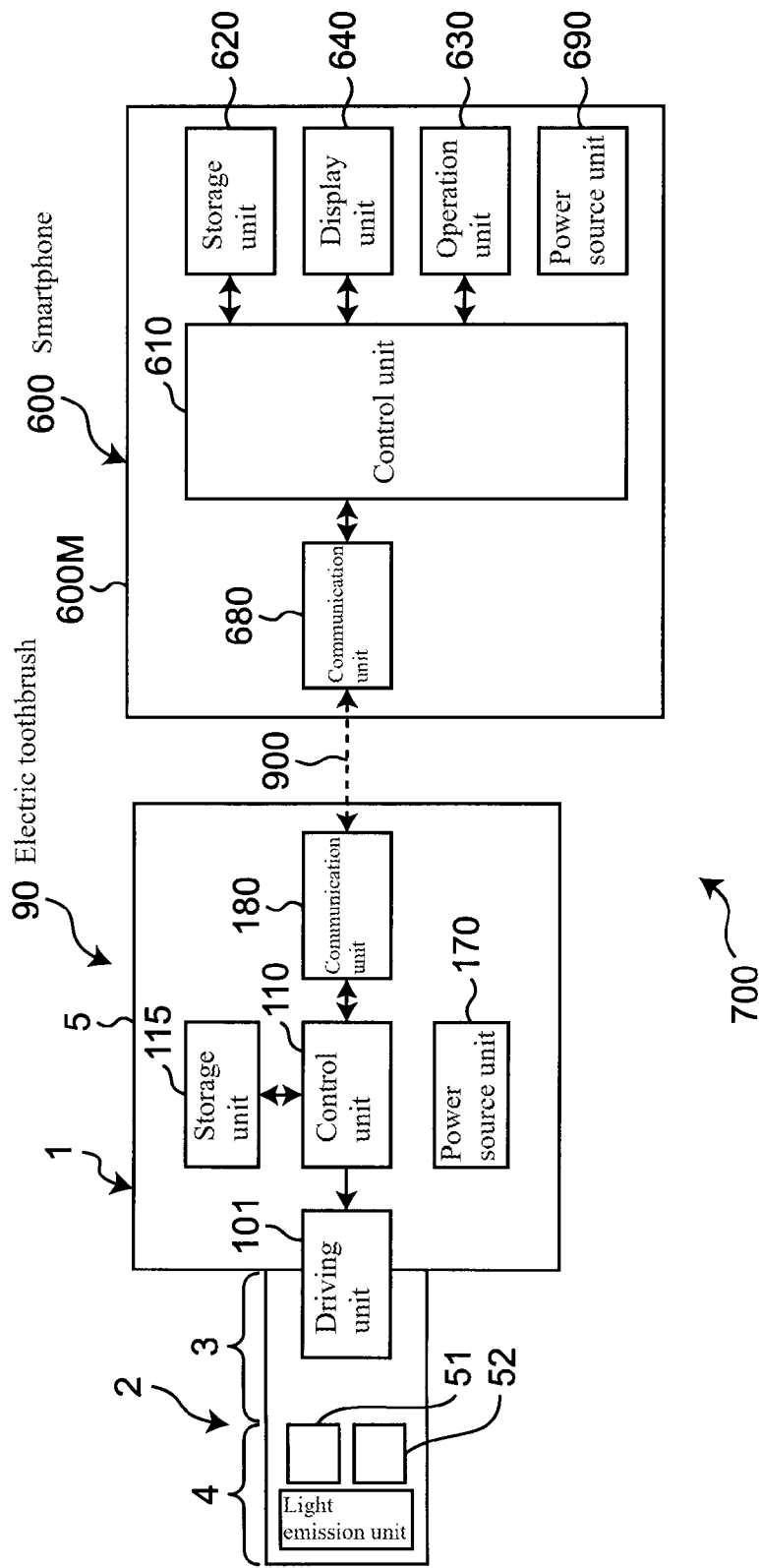
FIG. 8 is a diagram showing an example of the configuration of a system including the electric toothbrush and a smartphone.

FIG. 8 shows an example of the configuration of a system (the entirety of which is denoted by reference numeral 700) including the above-described electric toothbrush 90 and a smartphone 600. The system 700 includes the electric toothbrush 90 and the smartphone 600 serving as a computer apparatus such that they can communicate with each other in a wireless manner via a network 900.

The smartphone 600 includes a main body 600M, and a control unit 610, a storage unit 620, an operation unit 630, a display unit 640, a communication unit 680, and a power source unit 690 that are provided in the main body 600M. The smartphone 600 is a commercially available smartphone in which application software, which will be described later, has been installed.

The control unit 610 includes a CPU and its auxiliary circuit, and controls the units of the smartphone 600 and executes a process according to a program and data stored in the storage unit 620. For example, the control unit 610 processes data input from the communication unit 680 based on the instruction input via the operation unit 630, and causes the processed data to be stored in storage unit 620, displayed on the display unit 640, and output via the communication unit 680.

The storage unit 620 includes a RAM (random access memory) to be used as a workspace that is necessary for the control unit 610 to execute a program, and a ROM (read only memory) to be used to store a basic program executed by the control unit 610. Moreover, a semiconductor memory (e.g., a memory card or a SSD (solid state drive)) or the like may also be used as a storage medium of an auxiliary storage device for supplementing the storage area of the storage unit 620.

In this example, the operation unit 630 is constituted by a touch panel provided on the display unit 640. It should be noted that a hardware operating device such as a keyboard may be included.

In this example, the display unit 640 includes a display screen constituted by a LCD (liquid crystal display) or an organic EL (electroluminescence) display. With the display unit 640, various images are displayed on the display screen in accordance with the control performed by the control unit 610.

The communication unit 680 is configured so as to be capable of communicating with the electric toothbrush 90 in a wireless manner (e.g., using a BT communication or a BLE communication) via the network 900 in accordance with the control performed by the control unit 610.

In this example, the power source unit 690 includes a rechargeable battery, and supplies power to the units in the smartphone 600.

It is assumed that the user installs application software (referred to as "dental calculus display program") in the smartphone 600 in advance. This dental calculus display program is used to process the dental plaque/dental calculus data from the storage unit 115 of the electric toothbrush 90 and produce an image (referred to as "oral cavity chart") indicating the state inside the oral cavity of the user.

Figure 9:
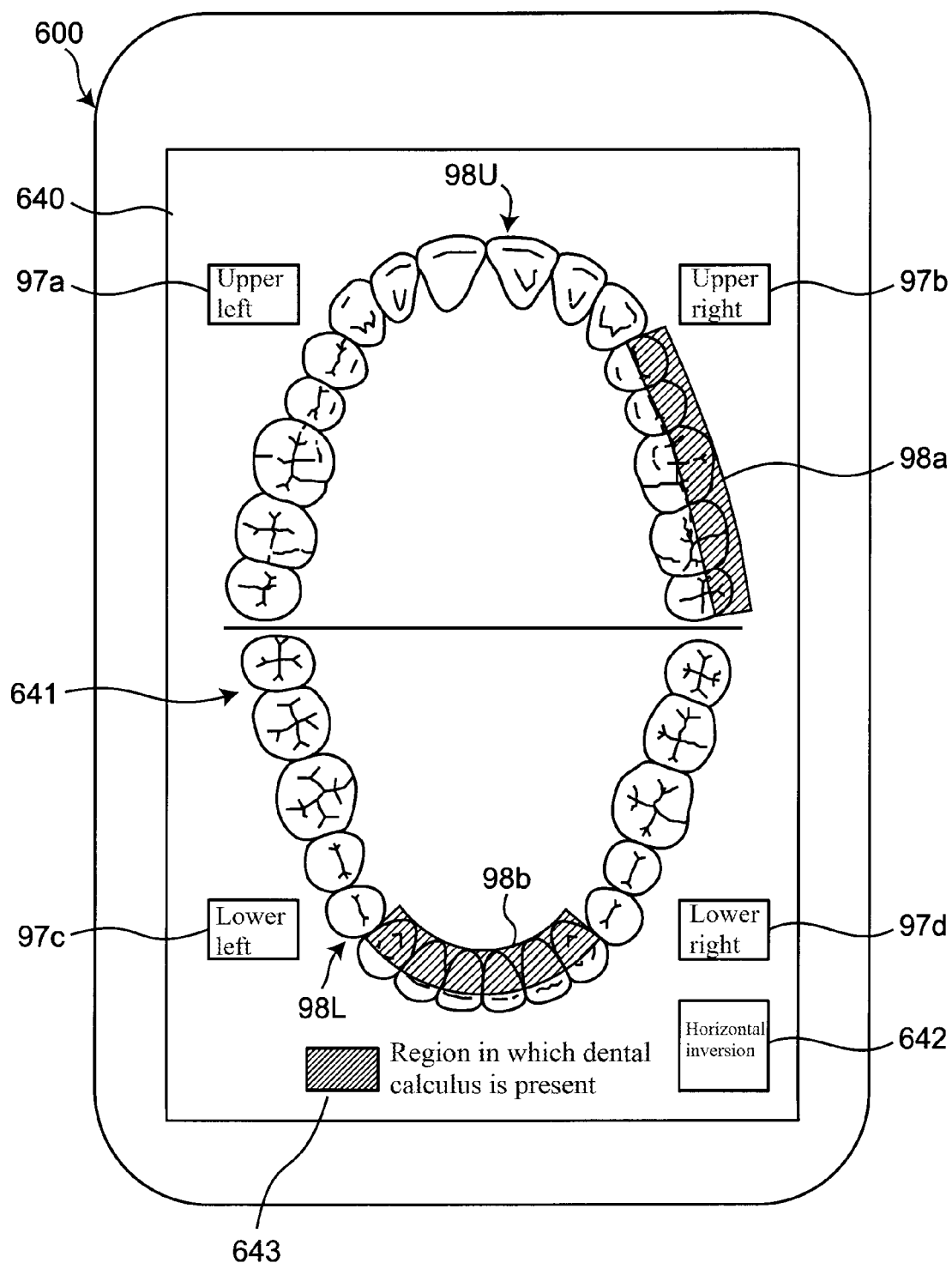
FIG. 9 is a diagram showing an example of an oral cavity chart displayed on a display unit of the smartphone.

Specifically, when the user starts the dental calculus display program, the communication unit 680 of the smartphone 600 receives the dental plaque/dental calculus data from the storage unit 115 of the electric toothbrush 90 via the network 900. Subsequently, the control unit 610 serves as a display processing unit and processes the dental plaque/dental calculus data and produces an oral cavity chart 641 indicating a region in which dental calculus is present in the user's tooth rows as shown in FIG. 9, for example. The oral cavity chart 641 produced by the control unit 610 is displayed on the display unit 640 (step S29 shown in FIG. 5).

Display Example

In the oral cavity chart 641 shown in FIG. 9, which corresponds to the content of the table of the dental plaque/dental calculus data in Table 2, regions in which dental calculus is present in upper and lower tooth rows 98U and 98L are denoted by marks 98a and 98b for distinguishing these regions from the other regions (in which dental calculus is not present). In this example, the marks 98a and 98b are indicated as a hatched closed area as shown in an illustration 643. Indicators 97a, 97b, 97c, and 97d that respectively indicate an "upper left side", an "upper right side", a "lower left side", and a "lower right side" of the tooth rows 98U and 98L are shown around the oral cavity chart 641. When the user sees the oral cavity chart 641, he/she can intuitively recognize that dental calculus is present on "maxillary right buccal side" and "mandibular anterior lingual side" of his/her tooth rows. Therefore, the user can appropriately determine whether or not he/she should have an examination and treatment from a dentist.

It should be noted that a mark indicating a region in which dental calculus is present is not limited to being indicated as a hatched area, and a stippled area, an area colored with a color different from that of the other areas, and the like are also possible.

Here, in the oral cavity chart 641 shown in FIG. 9, the left and right sides of the upper and lower tooth rows 98U and 98L correspond to the left and right sides of the user's body.

In such a case, a common user can intuitively recognize the region of his/her tooth rows in which dental calculus is present.

Figure 10:
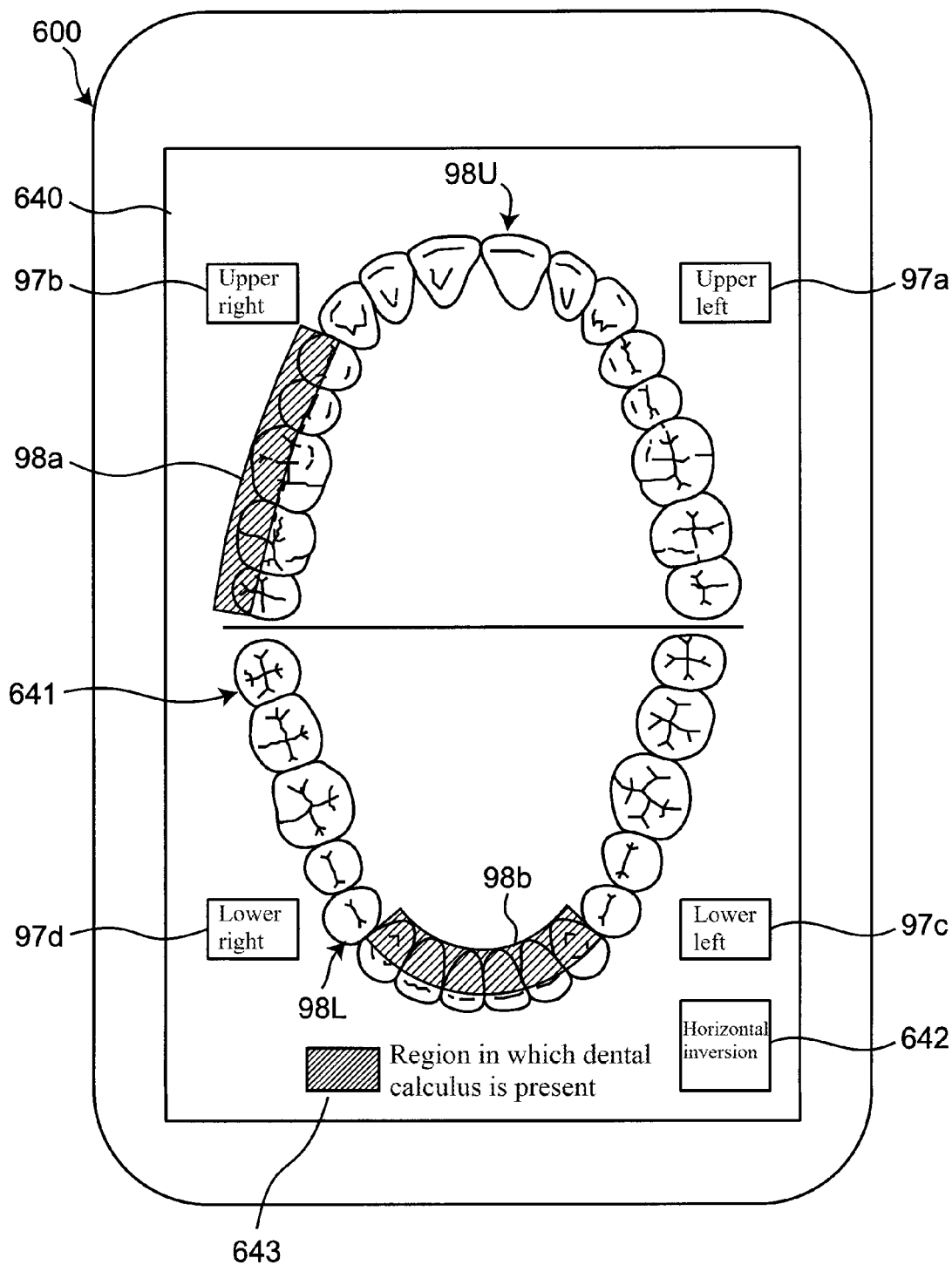
FIG. 10 is a diagram showing a display example obtained by horizontally inverting the oral cavity chart of FIG. 9.

As shown in FIG. 9, for example, a configuration may also be employed in which a horizontal inversion switch 642 is displayed together with the oral cavity chart 641 on the display unit 640, and the oral cavity chart 641 can be horizontally inverted depending on the selection of the user (through depression of the horizontal inversion switch 642). The reason for this is that in the dental field, the tooth rows of a patient are commonly indicated in the orientation as viewed from the front side of the patient. In such a case, as shown in FIG. 10, due to the oral cavity chart 641 being horizontally inverted, the indicator 97a indicating the "upper left side" and the indicator 97b indicating the "upper right side" are exchanged, and the indicator 97c indicating the "lower left side" and the indicator 97d indicating the "lower right side" are exchanged. Accordingly, when the user visits a dentist and asks for removal of dental calculus, showing an oral cavity chart in the orientation shown in FIG. 10 makes it easy to communicate with the dentist.

In addition, if a region in which "dental plaque is present" still remains in the user's tooth rows at the end of toothbrushing and the table of the dental plaque/dental calculus data includes information about that, the region in which dental plaque is present may be displayed in the oral cavity chart 641 together with a region in which dental calculus is present in the upper and lower tooth rows 98U and 98L. In such a case, it is desirable that a mark for indicating a region in which dental plaque is present can be distinguished from a mark for indicating a region in which dental calculus is present.

Moreover, the oral cavity charts 641 may also be stored in the storage unit 620 of the smartphone 600 chronologically for each production date. In this case, the user can operate the smartphone 600 via the operation unit 630 to cause the oral cavity charts 641 that are different in the production date to be displayed on the display unit 640 successively or simultaneously. Accordingly, the user can recognize the process through which dental calculus is deposited by referring to the oral cavity charts 641.

In the above-described embodiments, the control unit 110 of the electric toothbrush 90 functions as a detection unit and a determination unit, but there is no limitation thereto. A configuration may also be employed in which the control unit 610 functions as a detection unit and a determination unit with the electric toothbrush 90 and the smartphone 600 communicating with each other during toothbrushing. In such a case, the configuration of the control unit 110 of the electric toothbrush 90 can be simplified. This makes it possible to configure the control unit 110 with a logic IC (integrated circuit) instead of a CPU. Moreover, in such a case, it is desirable that the notification of the detection result (detected state) regarding whether or not dental plaque or dental calculus is present, and the notification of the presence of dental calculus are performed using the function of the smartphone 600 such as display on the display unit 640, voice from a speaker (not shown), or vibration caused by a vibrator (not shown).

An apparatus that serves as substantially a computer apparatus such as a tablet-type device, a personal computer, or the like may be used instead of the smartphone 600 in order to configure a system in combination with the electric toothbrush 90.

The foregoing embodiments are exemplary and various modifications are possible without departing from the scope of the present invention. The above-described multiple embodiments can be achieved independently or in combination with each other. Also, various features in different embodiments can be achieved independently, and features in different embodiments can be combined.

The invention claimed is:

1. A system comprising a toothbrush and a computer apparatus provided outside of the main body of the toothbrush,
wherein the toothbrush comprises:
a main body including a head portion having a bristle raising surface on which bristles are provided in a standing manner;
a light emitting diode that emits light through a specific region of the bristle raising surface to a tooth surface, and an optical filter member that receives radiated light from the tooth surface resulting from the light through the specific region, the light emitting diode and the optical filter member being provided in the main body; and
a processor that collectively detects whether or not a dental substance, the dental substance being at least one of dental plaque or dental calculus, is present on the tooth surface based on an output from the optical filter member, counts a predetermined time during brushing, and distinguishes whether the dental substance present on the tooth surface is the dental plaque or the dental calculus, wherein the dental plaque is a substance that can be removed by toothbrushing and the dental calculus is a substance that cannot be removed by toothbrushing,
wherein the processor starts to count the predetermined time in response to the detection of the dental substance during brushing, the predetermined period being sufficiently long to remove the dental plaque by brushing, but not long enough to remove the dental calculus, and
wherein the processor makes a distinguishing determination based on an expiration of the predetermined period and a detection of the dental substance after the expiration of the predetermined period that any remaining dental substance present on the tooth surface after expiration of the predetermined period is the dental calculus,
wherein the processor detects a brushing region brushed with the bristles; and
a memory in which data for each brushing region indicating whether or not the processor has determined that the dental calculus is present on the tooth surface is stored, and
a communication network that transmits the data stored in the memory to an external device from the main body; and
wherein the computer apparatus includes:
a computer communication network that receives data from the memory of the toothbrush;
a computer processor that processes the data from the memory and produces an image showing a region of the teeth in which the dental calculus is present; and
a display on which the image produced by the computer processor is displayed wherein the display shows an upper teeth row and a lower teeth row together with markings on the upper teeth row and the lower teeth row showing places where the dental calculus is present in the upper teeth row and the lower teeth row.

2. The system according to claim 1,
wherein the processor is provided in the main body.

3. The system according to claim 1, further comprising:
a motor that vibrates the head portion together with the bristles and is provided inside of the main body,
wherein the processor performs control for reducing an intensity of vibration performed by the motor when the processor determines that the dental calculus is present on the tooth surface.

4. The system according to claim 1, further comprising:
a notification unit that performs notification of a state detected by the processor or a result of determination by the processor.

5. The system according to claim 1, wherein the toothbrush reduces a vibration intensity when the processor determines that the dental calculus is present at the expiration of the predetermined period.

6. The system according to claim 4,
wherein when the processor determines that the dental calculus is present on the tooth surface, or when the state detected by the processor shifts from a state in which the dental plaque or the dental calculus is present to a state in which neither the dental plaque nor the dental calculus is present, the notification unit performs notification for prompting a change of a brushing region brushed with the bristles.

* * * * *